(12) United States Patent
Durant et al.

(10) Patent No.: US 12,415,888 B2
(45) Date of Patent: Sep. 16, 2025

(54) MULTIBRANCHED ACID TERMINATED OLIGOMERS OF ITACONIC ACID INCLUDING VINYLIDINE UNSATURATIONS

(71) Applicant: Itaconix Corporation, Stratham, NH (US)

(72) Inventors: Yvon Durant, Durham, NH (US); Madeleine Anderson, Lawrence, MA (US); John Shaw, Hampton Falls, NH (US)

(73) Assignee: ITACONIX CORPORATION, Stratham, NH (US)

( * ) Notice: Subject to any disclaimer, the term of this patent is extended or adjusted under 35 U.S.C. 154(b) by 661 days.

(21) Appl. No.: 17/658,532

(22) Filed: Apr. 8, 2022

(65) Prior Publication Data

US 2023/0323024 A1    Oct. 12, 2023

(51) Int. Cl.
  *C08G 63/672*    (2006.01)
(52) U.S. Cl.
  CPC .................................. *C08G 63/672* (2013.01)
(58) Field of Classification Search
  USPC ........................................................ 528/176
  See application file for complete search history.

(56) References Cited

U.S. PATENT DOCUMENTS

| | | |
|---|---|---|
| 11,766,394 B2 * | 9/2023 | Herrlein ................. A61K 8/895 424/70.12 |
| 2003/0232944 A1 | 12/2003 | Molenberg et al. |
| 2007/0009441 A1 | 1/2007 | Erathodiyil et al. |
| 2011/0183078 A1 | 7/2011 | Kano et al. |
| 2011/0217750 A1 | 9/2011 | Pandit et al. |
| 2012/0121841 A1 * | 5/2012 | Szkudlarek ........... C08F 283/01 528/304 |
| 2018/0223016 A1 * | 8/2018 | Tamareselvy .......... C11D 3/378 |

OTHER PUBLICATIONS

International Search Report and Written Opinion from corresponding PCT Appln. No. PCT/US2023/065424, dated Oct. 30, 2023.
Pubmed Compound Record for CID 90812917, "3-[(2S,3R,4R,5R)-2,3,4,5,6-pentakis[2-(carboxymethul) prop-2enoyloxy]hexoxy]carbonylbut-3-enoic acid", U.S. National Library of Medicine, Mar. 16, 2015, pp. 1-10.

* cited by examiner

*Primary Examiner* — Terressa Boykin
(74) *Attorney, Agent, or Firm* — Grossman, Tucker, Perreault & Pfleger, PLLC

(57) ABSTRACT

The present invention is directed at multibranched acid terminated oligomers of itaconic acid. Such multibranched acid terminated oligomers also contain six or more vinylidine groups providing unsaturations that can then be relied upon for subsequent Michael nucleophilic addition type reactions. The subject oligomers have particular use for treatment of damaged hair or skin.

16 Claims, No Drawings

MULTIBRANCHED ACID TERMINATED OLIGOMERS OF ITACONIC ACID INCLUDING VINYLIDINE UNSATURATIONS

FIELD

The present invention is directed at multibranched acid terminated oligomers of itaconic acid. Such multibranched acid terminated oligomers also contain six or more vinylidine groups providing unsaturations that can then be relied upon for subsequent Michael nucleophilic addition type reactions. Such Michael addition type reactions include reactions with available thiol or amine groups available in keratin and/or collagen proteins.

BACKGROUND

Itaconic acid is an unsaturated dicarboxylic organic compound. It has been utilized for the formation of acrylic type resins, acrylate latexes, as an absorbent, and in certain anti-scaling agents. Some of the polymerized methyl, ethyl, or vinyl esters of itaconic acid have been utilized in plastics, adhesives, elastomers and coatings.

When hair is bleached it can be otherwise damaged and become brittle or porous, and loose shine. As a consequence, a need exits to treat such damaged hair to assist in restoring its original properties. Skin can also suffer damage from excessive washing with soap or exposure to alcohol.

The present invention, among other things, is directed at multibranched acid terminated oligomers including 6 or more vinylidene groups, derived from itaconic acid, a hydroxy terminated polyol and a multifunctional hydroxy compound. Such oligomers may then be utilized to treat damaged hair or skin.

SUMMARY

A composition comprising a multibranched acid terminated oligomer including 6 or more vinylidene groups derived from itaconic acid, a hydroxy terminated polyol and a multifunctional hydroxy compound, wherein the oligomer is characterized by: (a) a maximum weight average molecular weight (Mw) of 30,000 g/mole; (b) a maximum number average molecular weight (Mn) of 10,000 g/mole; (c) an acid value of 100 mg KOH/gram to 250 mg KOH/gram; and (d) a hydroxyl value of less than or equal to 35 mg KOH/gram.

A method of forming a multibranched acid terminated oligomer including 6 or more vinylidene groups comprising reacting itaconic acid, a hydroxy terminated polyol and a multifunctional hydroxy compound, in the presence of a free-radical inhibitor, wherein itaconic acid is present in molar excess to said hydroxy terminated polyol and said multifunctional hydroxy compound and forming the multibranched acid terminated oligomer including six or more vinylidene groups, wherein the oligomer is characterized by: (a) a maximum weight average molecular weight (Mw) of 30,000 g/mole; (b) a maximum number average molecular weight (Mn) of 10,000 g/mole; (c) an acid value of 100 mg KOH/gram to 250 mg KOH/gram; and (d) a hydroxyl value of less than or equal to 35 mg KOH/gram.

A method of treating hair comprising: (1) supplying a multibranched acid terminated oligomer including 6 or more vinylidene groups, derived from itaconic acid, a hydroxy terminated polyol and a multifunctional hydroxy compound, wherein said oligomer is characterized by: (a) a maximum weight average molecular weight (Mw) of 30,000 g/mole; (b) a maximum number average molecular weight (Mn) of 10,000 g/mole; (c) an acid value of 100 mg KOH/gram to 250 mg KOH/gram; and (d) a hydroxyl value of less than or equal to 35 mg KOH/gram; and (2) treating hair with said multibranched acid terminated oligomer including 6 or more vinylidene groups.

A method of treating skin comprising: (1) supplying a multibranched acid terminated oligomer including 6 or more vinylidene groups, derived from itaconic acid, a hydroxy terminated polyol and a multifunctional hydroxy compound, wherein said oligomer is characterized by: (a) a maximum weight average molecular weight (Mw) of 30,000 g/mole; (b) a maximum number average molecular weight (Mn) of 10,000 g/mole; (c) an acid value of 100 mg KOH/gram to 250 mg KOH/gram; and (d) a hydroxyl value of less than or equal to 35 mg KOH/gram; and (2) treating skin with said multibranched acid terminated oligomer including 6 or more vinylidene groups.

DETAILED DESCRIPTION OF PREFERRED EMBODIMENTS

The present invention is directed at multibranched acid terminated oligomers of itaconic acid. Such multibranched acid terminated oligomers also contain six or more vinylidine groups providing unsaturation that can then be relied upon for subsequent Michael nucleophilic addition type reactions. Itaconic acid is therefore preferably provided at an excess molar ratio to selected hydroxy-terminated polyols in combination with multifunctional hydroxy compounds, in the presence of a free-radical inhibitor, to provide the branched acid terminated oligomers including six or more vinylidene (unsaturated) groups. More specifically, the multibranched acid terminated oligomers include ester linkages between the reacted carboxylic acid groups of itaconic acid and the hydroxy groups of the polyol and multifunctional hydroxy compound. The multibranched acid terminated oligomers are also preferably configured to be water soluble.

The hydroxy terminated polyol utilized to form the multibranched acid terminated oligomers with six or more vinylidene groups preferably have the following general structure, in the preferred situation where the average functionality of the hydroxy group is 2.0:

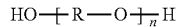

In the above, R is preferably an alkyl group (only carbon and hydrogen atoms). More specifically, such alkyl groups have 2-3 carbon atoms and hydrogen (e.g., —$CH_2CH_2$—, —$CH_2CH_2CH_2$—, or —$CH_2CH(CH_3)$—, which one would recognize as an ethyl, propyl or isopropyl type repeating unit structure.

It can therefore be appreciated that preferably, the hydroxy terminated polyol preferably is a polyether polyol. The hydroxy terminated polyol herein is also preferably one that indicates an average functionality of the hydroxy group in the range of 1.8 to 2.2. Average functionality is reference to the number of hydroxy groups in the hydroxy terminated polyol that participate in reaction with the carboxylic group of itaconic acid. The value of n in the above may preferably be in the range of 2-20, more preferably 3-10, and even more preferably, 3-5. One particularly preferred hydroxy terminated polyol herein is therefore poly(ethylene glycol) with an average functionality of 2.0. Polyethylene glycol is commercially available as PEG 200, with a molecular weight in the range of 190-210 and with a range of average hydroxyl number, mg KOH/g, of 535-590.

In addition, the itaconic acid herein is reacted in the presence of one or more multifunctional hydroxy compounds having the following general structure:

The R group in the above multifunctional hydroxy compound may again be an alkyl group, having 3-12 carbon atom. The value of n in the multifunctional hydroxy compound is greater than 2 up to 8. Preferred multifunctional hydroxy compounds therefore include glycerol, trimethyolpropane, xylitol, erythritol, maltitol, sorbitol, isomalt and/or pentaerythritol. Accordingly, the multifunctional hydroxy compound can preferably be selected from C-5 or C-6 carbohydrates, in cyclic or linear form, wherein C-5 or C-6 is reference to the number of carbon atoms in the carbohydrate, also containing hydrogen and oxygen atoms. Such carbohydrates may therefore include monosaccharides (simple sugars), such as glucose, galactose, talose, idose, mannose, altrose, allose, fructose, sorbose, tagatose, xylose, ribose, lyxose, arabinose, and disaccharides, composed of two monosaccharides, such as sucrose, lactose, maltose, isomaltulose, trehalose or cellobiose. These multifunctional hydroxy compounds can therefore promote the formation of a multibranched acid terminated oligomer of itaconic acid.

The multibranched acid terminated oligomers having six or more vinylidene groups herein are also those that are preferably characterized by having one or more of the following molecular weight features: (1) a maximum weight average molecular weight or Mw value of 30,000 g/mole; (2) a maximum number average molecular weight value or Mn of 10,000 g/mole; (3) a Mw value in the range of 950 g/mole to 30,000 g/mole, preferably 1500 g/mole to 18,000 g/mole, even more preferably 1800 g/mole to 9000 g/mole and/or (4) a Mn value in the range of 800 g/mole to 10,000 g/mole, preferably 1200 g/mole to 6000 g/mole, even more preferably 1400 g/mole to 3000 g/mole. The value of Mw/Mn may therefore preferably fall in the range of 1.2 to 3.0, which is reflective of the molecular weight distributions for the subject oligomers.

It may therefore now be appreciated that one preferred example of a multibranched acid terminated oligomer with six (6) vinylidene groups that can be formed herein includes the reaction of itaconic acid with poly(ethylene glycol) and glycerol, wherein the itaconic acid is employed at a molar excess to the combined molar quantities of poly(ethylene glycol) and glycerol. For example, one may preferably combine 6.0 moles of itaconic acid with 3 moles of poly(ethylene glycol) and 1 mole of glycerol to promote the formation of the following multibranched acid terminated oligomer with six or more vinylidene groups:

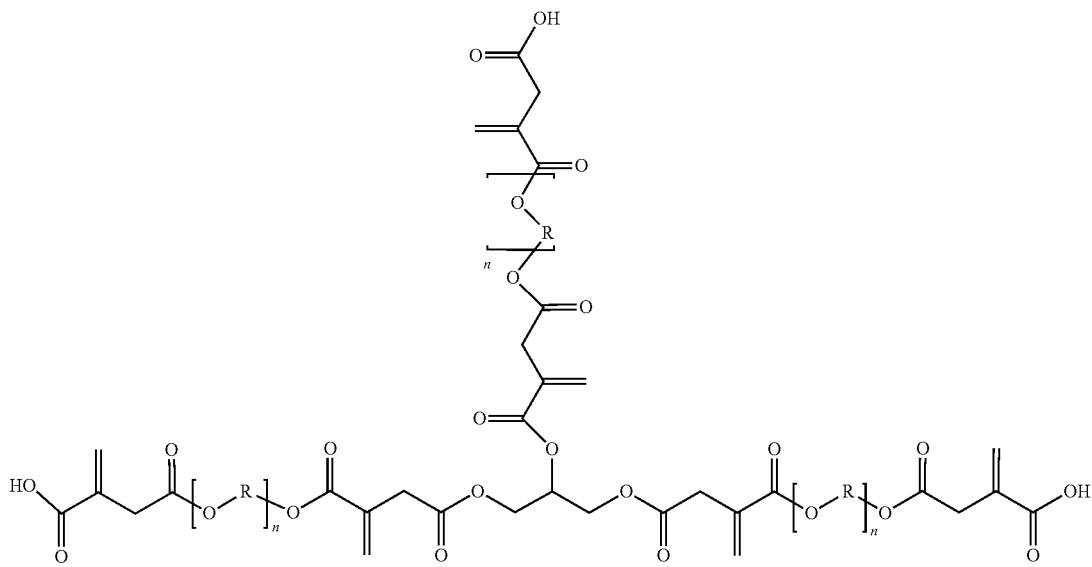

In the above R is therefore —CH$_2$CH$_2$—. In addition, as can be seen, there are three (3) branches extending from the reacted glycerol where each branch includes poly(ethylene glycol), each with an end group containing carboxylic acid functionality (—COOH) and each branch provides at least two units of residual unsaturation in the form of a vinylidene group:

Accordingly, as illustrated above, reference to a multibranched acid terminated oligomer herein is reference to a minimum of three (3) branches. However, the number of branches that may be present, which extend from the use of the multifunctional hydroxy compound, can preferably range from 3-20, including any individual values or increments therein. For example, the number of branches can preferably range from 3-10, or 3-6, or even 3-5. In addition, preferably as noted, the subject oligomers herein contain at least six (6) or more vinylidine groups per oligomer, more preferably 6-12 vinylidine groups per oligomer, or even 6-8 vinylidine groups per oligomer.

Another preferred example of a multibranched acid terminated oligomer that can be formed herein includes the reaction of itaconic acid in molar excess with poly(ethylene glycol) to the combined molar quantities of poly(ethylene glycol) and pentaerythritol to promote the formation of the following multibranched acid terminated oligomer:

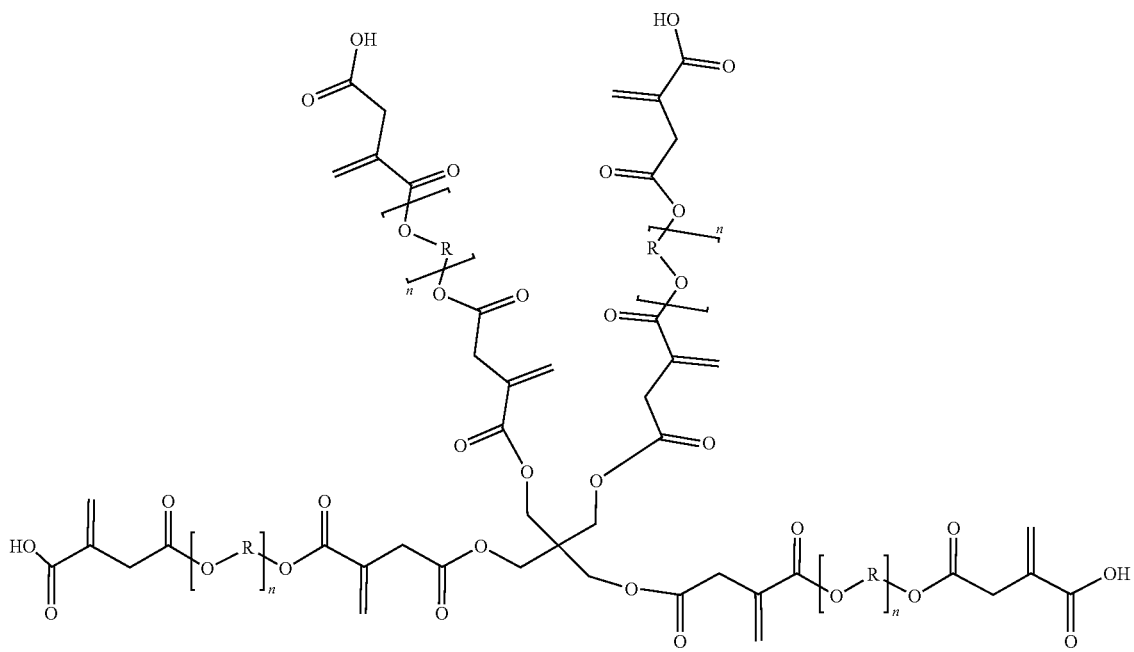

In the above R is once again preferably —CH$_2$CH$_2$—. In addition, as can be seen, there are four (4) branches now extending from the reacted pentaerythritol where each branch includes poly(ethylene glycol), along with an end group containing carboxylic acid functionality (—COOH) and again, unsaturation in the form of a vinylidene group (—C=CH$_2$). As can be seen, this preferred oligomer now contains 8 vinylidine groups. Moreover, to form the above a multibranched acid terminated oligomer one may preferably combine 8.0 moles of itaconic acid to 4 moles of poly(ethylene glycol) with 1 mole of pentaerythritol. As can be seen from the above, there are four (4) branches extending from the pentaerythritol multifunctional hydroxy compound.

Yet another preferred example of a multibranched acid terminated oligomer with vinylidine unsaturation that can be formed herein includes the reaction of itaconic acid in molar excess with poly(ethylene glycol) to the combined the molar quantities of poly(ethylene glycol), glycol and pentaerythritol:

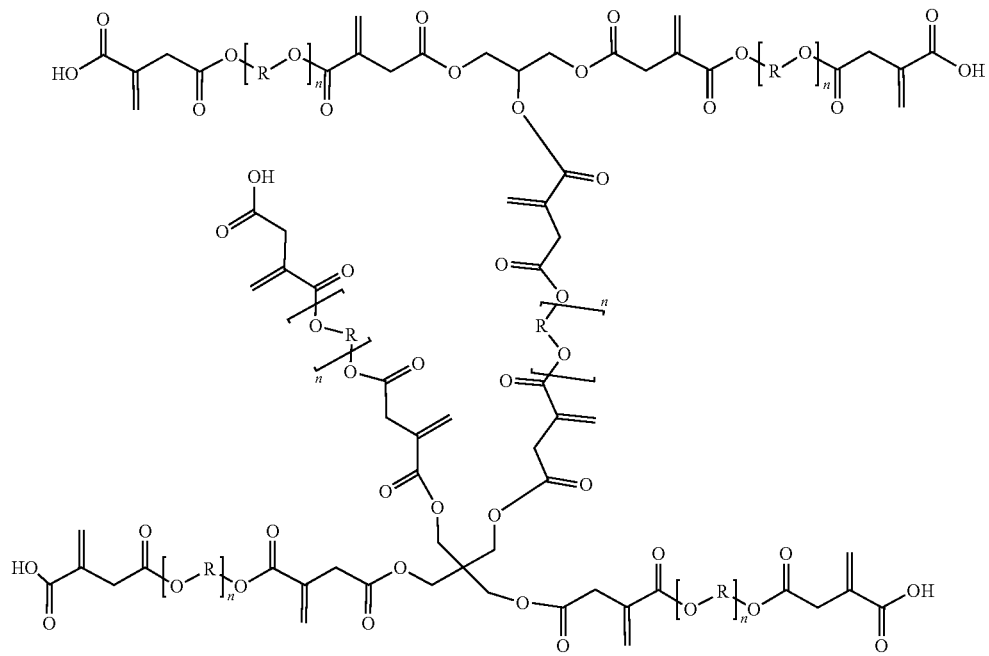

In the above R is once again preferably —CH$_2$CH$_2$—. In addition, as can be seen, there is again terminal carboxylic acid functionality (—COOH) and unsaturation in the branches in the form of a vinylidene group (—C=CH$_2$). The total number of vinylidene groups in the above oligomer now total 12. Moreover, to form the above multibranched acid terminated oligomer with 12 vinylidine unsaturated groups, one may preferably combine 12 moles of itaconic acid with 6 moles of poly(ethylene glycol) and 1 mole of pentaerythritol and 1 mole of glycerol. In the above structure, it can also be seen that there is an interconnecting chain segment with ester linkages present at one former hydroxy location on the pentaerythritol and one former hydroxy location of the glycerol. In the broad context of the present invention, the number of interconnecting chain segments that may occur between the multifunctional hydroxy compound is preferably in the range of 0-2, meaning 0 interconnects, 1 interconnect, or 2 interconnects.

In addition, it should be added that in the above referenced exemplary and preferred reaction schemes resulting in the formation of the multibranched acid terminated oligomers with 6 or more vinylidene groups, they are prepared in the presence of a free-radical inhibitor. The free-radical inhibitor is understood as a compound that prevents unwanted free-radical reaction of the unsaturation (carbon-carbon double bond) present on itaconic acid. Such unwanted reaction therefore includes free-radical polymerization. The free-radical inhibitors preferably are selected from one or more of methyl ether hydroquinone (MEHQ), hydroquinone (HQ), tertiobutylhydroquinone, or tertiobutylcatechol. The concentration of the free-radical inhibitor that is preferably present when forming the multibranched acid terminated oligomers herein with terminal six or more vinylidene groups, is preferably in the range of 10 ppm to 3,000 ppm, more preferably 50 ppm to 2,000 ppm, and even more preferably 100 ppm to 1,000 ppm.

Another preferred characterizing feature of the multibranched acid terminated oligomers herein with vinylidene unsaturation are their acid-values and the hydroxyl value. Acid value is reference to the mass of potassium hydroxide (KOH) in milligrams that is required to neutralize one gram of the multibranched acid terminated oligomers with vinylidene unsaturation. Hydroxyl value is reference to the number of milligrams of potassium hydroxide required to neutralize the acetic acid taken up on acetylation of one gram of the multibranched acid terminated oligomers with vinylidene unsaturation that may contain some free hydroxy groups. The multibranched acid terminated oligomers herein with vinylidene unsaturation therefore preferably indicate the following characterizing features: (1) an acid value (AV) in the preferred range of 100 mg KOH/gram to 250 mg KOH/gram, more preferably 100 mg KOH/gram to 200 mg KOH/gram; and/or (2) a hydroxyl value of less than or equal to 35 mg KOH/gram, more preferably less than 20 mg KOH/gram.

A still further preferred characterizing feature of the multibranched acid terminated oligomers herein with vinylidene unsaturation is their water solubility. Such water solubility is promoted by placement of the oligomers into water followed by neutralization with an inorganic or organic base to form an acid salt, such as sodium or potassium hydroxide. Reference to an acid salt present in the oligomers herein is therefore reference to a carboxylic acid group that is present in the form of —COO$^-$M$^+$ wherein M includes sodium or potassium. Examples of organic bases preferably include organic amines, such as primary, secondary or tertiary amines formed via the use of alkyl groups. Reference to an acid salt structure present in the oligomers herein that is sourced from an organic base therefore includes —COO$^-$(NR$_3$)$^+$ where R is an alkyl group having 2-3 carbon atoms or an alkyl alcohol. For example, triethyl amine, triethanol amine and/or trimethyl amine. In the case of triethanol amine as the neutralization reagent, a representative example of the multibranched acid terminated oligomer herein with vinylidine unsaturated groups, that is water soluble, would be as follows:

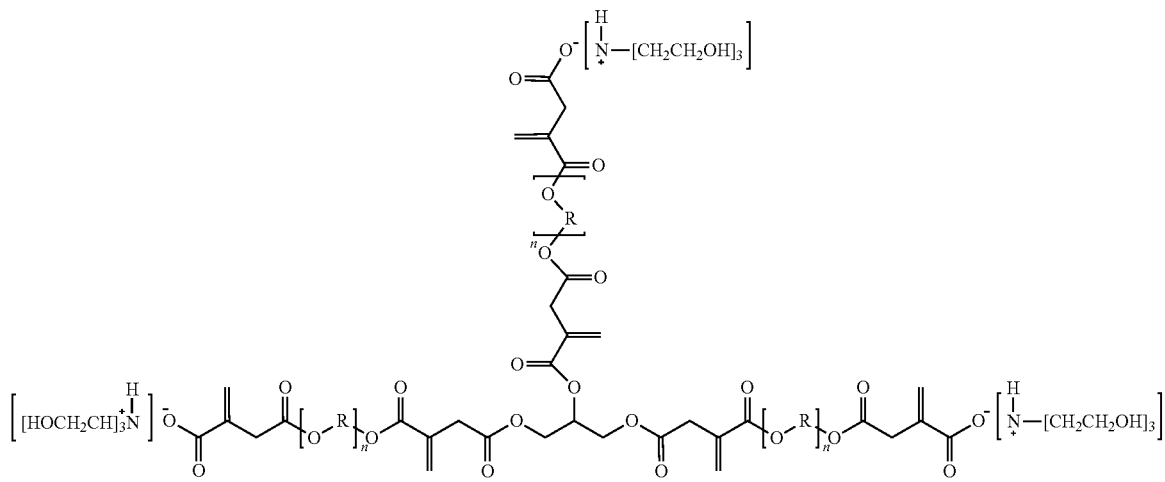

As alluded to above, the multibranched acid terminated oligomers herein with vinylidene unsaturation that are made water soluble in the form of an acid salt, are capable of undergoing Michael nucleophilic addition type reactions. In particular, Michael nucleophilic addition type reactions between the vinylidene groups with available thiol or amine groups in keratin and/or collagen proteins. In that regard, keratin is recognized as a fibrous structural protein that forms the structural component of hair. It includes an amino acid composition and sequence with a relatively high concentration of cysteine that forms inter- and intra-molecular disulfide bonds. The structure of cystine in an amino acid sequence showing a disulfide bond (—S—S—) joining two cysteine residues is provided below:

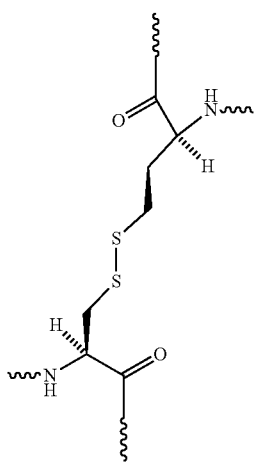

Accordingly, the vinylidene unsaturation groups in the multibranched acid terminated oligomers herein can undergo: (1) a Michael addition with the primary amines present in keratin and or collagen; and/or (2) a Michael addition with a thiol (—SH) group that may be available in damaged keratin or damaged collagen.

By way of one representative example, below is the result of a Michael addition of the primary amine present in the lysine amino acid component of keratin, with one vinylidine unsaturated group in the multibranched acid terminated oligomers herein, that has been made water soluble by treatment with triethanol amine:

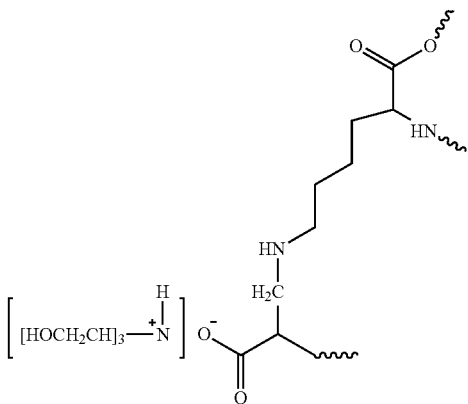

Similarly, below is the result of a Michael addition of the primary amine present in the arginine amino acid component of keratin, with one vinylidine unsaturated group in the multibranched acid terminated oligomers herein, that has been made water soluble by treatment with triethanol amine:

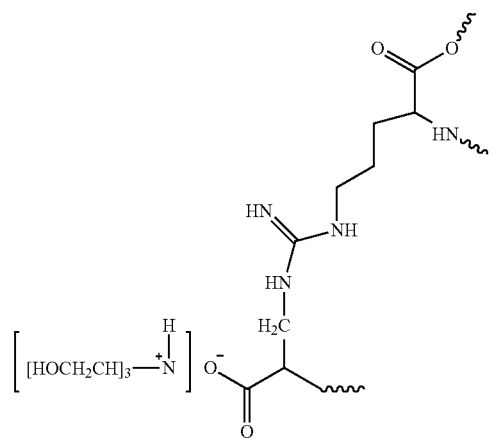

The multibranched acid terminated oligomers herein including 6 or more vinylidene groups therefore find particular utility for use in hair care and skin care, more specifically to improve hair strength, appearance (smoothness and shine) and skin softness.

WORKING EXAMPLES

Example 1

To a round bottom flask reactor with a magnetic stirrer, a dean-stark condenser, was added: itaconic Acid, 30.22 gr, glycerol 3.73 gr, tetraethylene glycol 22.67 gr, MEHQ 0.058 gr. Heat was set to 120° C. with an electric mantel. When the temperature reached 120° C., titanium tetrabutoxide 0.216 gr was added. Temperature was increased by 20° C. per hour until 200° C., then held at 200C for 20 minutes. Vacuum (~30 mmHg) was applied for 20 minutes, then heat was turned off.

After cooling to room temperature (RT) a 50 wt % solution was prepared in water and neutralized with KOH to pH 4.5. The resulting solution was amber clear and homogenous. Molecular weight analysis by GPC gave a weight average molecular weight of 1500 g/mole and a number average molecular weight of 1135 g/mole. Acid Number titration gave an AV=149 mg KOH/g.

Example 2

To a round bottom flask reactor with a magnetic stirrer, a dean-stark condenser, was added: itaconic Acid, 30.22 gr, xylose 5.84 gr, tetraethylene glycol 22.54 gr, MEHQ 0.065 gr. Heat was set to 120° C. with an electric mantel. When the temperature reached 120° C., titanium tetrabutoxide 0.225 gr was added. Temperature was increased by 20° C. per hour until 200° C., then held at 200C for 20 minutes. Vacuum (~30 mmHg) was applied for 20 minutes, then heat was turned off.

After cooling to RT a 50 wt % solution was prepared in water and neutralized with KOH to pH 4.5. The resulting solution was very dark and homogenous. Molecular weight analysis by GPC gave a weight average molecular weight of 970 g/mole and a number average molecular weight of 845 g/mole. Acid Number titration gave an AV=244 mg KOH/g.

Example 3

To a round bottom flask reactor with a magnetic stirrer, a dean-stark condenser, was added: Itaconic Acid 30.30 gr, glucose 7.01 gr, tetraethylene glycol 22.63 gr, MEHQ 0.055 gr. Heat was set to 120° C. with an electric mantel. When the temperature reached 120° C., titanium tetrabutoxide 0.204 gr was added. Temperature was increased by 20° C. per hour until 200° C., then held at 200C for 20 minutes. Vacuum (~30 mmHg) was applied for 20 minutes, then heat was turned off.

After cooling to RT a 50 wt % solution was prepared in water and neutralized with KOH to pH 4.5. The resulting solution was very dark and homogenous. Molecular weight analysis by GPC gave a weight average molecular weight of 1000 g/mole and a number average molecular weight of 890 g/mole. Acid number titration gave an AV=198 mg KOH/g.

Example 4

To a round bottom flask reactor with a magnetic stirrer, a dean-stark condenser, was added: itaconic Acid, 561.72 gr, glycerol 65.83 gr, tetraethylene glycol 418.84 gr, pentaerythritol 0.7 gr, MEHQ 1.053 gr. Heat was set to 120° C. with an electric mantel. When the temperature reached 120° C., titanium tetrabutoxide 1.3 gr was added. Temperature was increased by 20° C. per hour until 200° C. Vacuum (~30 mmHg) was applied for 30 minutes, then heat was turned off.

After cooling down to 50° C., 886 gr of water was added, then 113.1 gr of potassium hydroxide at 45 wt % was added. The resulting solution had a yellow color, a moisture content of 50.14%, a pH=4.5, a turbidity of 11 and a viscosity of 22 cP. Molecular weight analysis by GPC gave a weight average molecular weight of 2400 g/mole and a number average molecular weight of 1600 g/mole. Acid number titration gave an AV=137 mg KOH/g.

When a solution of Example 4, at 2.5 wt % to 10 wt % of the oligomer herein is tested with the Hair Protein Loss method (see below), a protein loss of 26+/−2 mg/g was determined. For comparison, unbleached hair has a zero mg/g protein loss, a freshly bleached hair has a protein loss of 90 mg/g, and a bleached, then washed hair has a 42 mg/g protein loss.

Example 5

To a round bottom flask reactor with a magnetic stirrer, a dean-stark condenser, was added: itaconic Acid 29.23 gr, glycerol 0.08 gr, tetraethylene glycol 22.09 gr, pentaerythritol 5.05 gr, MEHQ 0.07 gr. Heat was set to 120° C. with an electric mantel. When the temperature reached 120° C., tetraisopropylorthotitanate 0.261 gr was added. Temperature was increased by 20° C. per hour until 200° C. Then vacuum at 30 mtorr was applied for 30 minutes, followed by a cool down to RT Molecular weight analysis by GPC gave a weight average molecular weight of 5500 g/mole and a number average molecular weight of 2100 g/mole.

Example 6

To a round bottom flask reactor with a magnetic stirrer, a dean-stark condenser, was added: Itaconic Acid 224.60 gr, glycerol 26.51 gr, tetraethylene glycol 167.51 gr, pentaerythritol 0.28 gr, MEHQ 0.4 gr. Heat was set to 120° C. with an electric mantel. When the temperature reached 120° C., tetraisopropylorthotitanate 1.28 gr was added. Temperature was increased by 20° C. per hour until 200° C. Then vacuum at ~30 mtorr was applied for 30 minutes.

After cooling to 50° C., 347 gr of water was added, then 42.51 gr of potassium hydroxide at 45 wt % was added. The resulting solution had a pH=5. Acid number titration gave an AV=131 mg KOH/g. Molecular weight analysis by GPC gave a weight average molecular weight of 2400 g/mole and a number average molecular weight of 1250 g/mole Example of Formulations For Application To Hair Care Foaming Solution The following ingredients were mixed together using a mechanical stirrer at room temperature. Solution from Example 4, 4 gr, water deionized by reverse osmosis 13 gr, sodium hydroxide 1 molar 3 gr, phenoxyethanol and caprylyl glycerol 0.1 gr, decyl glucoside 0.1 gr, Polysorbate 20 0.1 gr. The resulting solution was clear, and creates a stable foam, particularly when using a foaming hand pump dispenser. The resulting foaming solution can be applied on hair either after a hair coloring treatment, or a as a maintenance treatment before or after shampooing hair. It can also be used as a light maintenance shampoo.

Bond Restorer

The following ingredients were mixed together using a mechanical stirrer at room temperature. Solution from Example 4 20 gr, water deionized by reverse osmosis 79.5 gr, sodium hydroxide 0.63 gr, potassium sorbate 0.4 gr. The resulting solution was clear and can be applied on hair either during or after a hair coloring treatment in order to strengthen the hair and/or the shine of the hair.

Conditioner

The following ingredients were mixed together using a mechanical stirrer. First all the materials of phase one are heated to 70C and mixed together. Separately the components of phase 2 are heated to 70C and mixed together. Then phase 2 is added to phase one continuously over 30 seconds then further mixed until a homogeneous cream is obtained. Last the components of phase 3 are added.

|  | Amount (gr) |
|---|---|
| Phase 1 | |
| Deionized Water | 82 |
| Panthenol | 0.1 |
| Tetrasodium glutamate diacetate | 0.1 |
| Phase 2 | |
| Cetearyl Alcohol | 4 |
| 1,2 propanediol | 2 |
| Cetearyl ethylhexanoate, isopropyl myristate | 3 |
| Stearamidopropyl dimethylamine | 1 |
| Behentrimonium chloride | 1 |
| Avocado oil | 0.5 |
| Phase 3 | |
| Caprylyl glycol and phenylpropanol | 0.3 |
| Example 4 | 4 |
| Lactic acid | q.s pH 5 |

The resulting formulation can be applied on hair as a hair conditioner.

Performance Testing

Hair Treatment Process 0.4 g of hair tress is weighed and tied together then 1 g of treatment (oligomers directly or bond restorer or conditioner formulations described above containing the oligomers) is applied to hair with a pipette ensuring saturation of all hair strands. The hair sample is sealed in a plastic and left for 30 minutes. Tress is then rinsed 7 times with water using a laboratory wash bottle, then 0.3 g of a 5% sodium lauryl sulfate solution is applied and massaged into the hair for 30 seconds. The tress is then rinsed 7 times with water from a laboratory wash bottle and then 0.4 g of dilute lactic acid (pH 5) is added to the hair tress and left for 30 seconds then rinsed 7 times with water from a laboratory wash bottle and the final hair tress is left to dry overnight.

Hair Protein Loss Analysis Process 0.2 g of hair (treated herein, untreated or damaged) is cut into ¼ in pieces then weighed into 50 ml sterile plastic jar followed by 15 g of water to suspend the hair. The exact total weight is recorded, then the jar is sealed and put into a floor shaker at a pre-set speed and shaken for 4 hours. Then 0.5 g of supernatant is weighed into glass vials and 0.5 g of 1 M NaOH is added and left to sit for 30 minutes to dissolve the protein in suspension. Then 1 g of $CuCO_3$ solution* is added and left to sit for 15 minutes followed by the addition of 3 g of Folin-phenol solution** and left to sit for 40 minutes. The exact weights of all components are recorded for calculations. Absorbance of the solution is then measured using an Agilent 8453 spectrophotometer at 750 nm in a 10 ml glass cell. Protein concentration was calculated from a standard curve using hydrolyzed keratin as a standard (protein conc. Wt %=(slope×abs @ 750 nm)−intercept). This value was then used to calculate the total protein loss in mg per g of hair. Larger protein loss values are associated with greater hair damage.

Cu-carbonate solution prepared by mixing 20 g of 10% $Na_2CO_3$, 1 g of 2% potassium tartrate and 1 g of 1% $CuSO_4$ Folin-Phenol solution prepared by dilution of 5 g of 2 N Folin-Phenol with 45 g of RO water Turbidity A HI 93703 Portable Microprocessor Turbidity Meter was used. The instrument is calibrated at 0 FTU using HPLC grade water as a standards and at 10 FTU using Calibration standard HI93703-10.

Moisture Content

A moisture scale analyzer is used. It records weight as function of time, while maintaining the sample at 110° C. using an infrared heater. When a constant weight is recorded for 30 seconds, the test is completed and the weight recorded as a percent decrease from the initial weight. All moisture contents are expressed as weight percent.

Determination of pH

All pHs are reported in at room temperature. The pH probe is a Tris-Compatible flat sensor. The pH meter is calibrated using pH4 and pH=7 standard solutions prior to any measurement reading.

Acid Number

This method provides a standard characterization of the residual amount of acid in an ester or polyester. This method is most suited for non-aqueous materials.

Solvent preparation: Prepare the solvent by mixing 2 parts toluene with 1 part anhydrous ethanol. Add 3 drops of phenolphthalein indicator (1% in ethanol) to solvent mix.

Sample preparation: Weigh 0.2 g of sample into titration beaker, add 40 g of solvent and mix until completely dissolved. Add 3 drops of Phenolphthalein indicator (1% in ethanol) to sample.

Titration of Sample

Place the titration beaker with a magnetic stir bar on a stir plate and stir at a medium speed. Fill a burette with 0.1M KOH in ethanol and position the burette over the test solution. Begin titration by adding the titrant at a rate of approximately 1 mL/min with stirring, stop when sample turns pink for at least 10 seconds and record the volume of titrant used (V1).

Titration of blank sample: Run the titration method on the blank solvent and record titer (V2).

Calculations and Reporting For All Methods of Determination

Acid Value (AV) Calculation $$AV = 56.1*(V1-V2)*c/m$$

Where:

$V_1$=Volume in ml of KOH used to neutralize the test solution $V_2$=Volume in ml of KOH used to neutralize blank determination c=Concentration in moles per liter of the KOH solution m=Mass in grams of the test portion 56.1=Is a constant (molar mass of KOH in g/mol)

Molecular Weight Determination

Gel Permeation Chromatography (GPC) was used to determine molecular weights. The GPC is first equilibrated with the eluent (HPLC-grade Tetrahydrofuran—THF) through three VISCOTEK GPC columns (LT4000L, T2000 and LT5000L) for approximately one hour. A refractive index detector (RID) is used to measure signal concentration. The RID is purged for 20 minutes before sample analysis is started. The following instrument conditions are used: Eluent: HPLC-grade THF with inline degasser; Flow Rate: 1.0 mL/min; Run Time: 45 min; Injection volume: 100 µL; Draw/Eject Speed: 200 µL/min; RID Optics Temperature: 40° C.; Automatic Purge: 1 min; Column Temperature: 35° C.

A 1 wt. % polymer solution is prepared using the GPC eluent solution as solvent. This solution is filtered with a 0.204 syringe-tip filter into a 2 mL HPLC vial which is then crimped closed. The vial is placed into the GPC autosampler and the chromatographic run is initiated. Molecular weight calibration was done using 9 polystyrene standards with molecular weights ranging from 589 g/mole to 1,800,000 g/mole. The 9 standards were used to create a third order polynomial correlation between peak elution time and molecular weights. Each unknown sample is evaluated using this calibration function.

What is claimed is:

1. A composition comprising a multibranched acid terminated oligomer including 6 or more vinylidene groups, derived from itaconic acid, a hydroxy terminated polyol and a multifunctional hydroxy compound, wherein said oligomer is characterized by: (a) a maximum weight average molecular weight (Mw) of 30,000 g/mole; (b) a maximum number average molecular weight (Mn) of 10,000 g/mole; (c) an acid value of 100 mg KOH/gram to 250 mg KOH/gram; and (d) a hydroxyl value of less than or equal to 35 mg KOH/gram;

wherein said multibranched acid terminated oligomer including 6 or more vinylidene groups comprises the following structure:

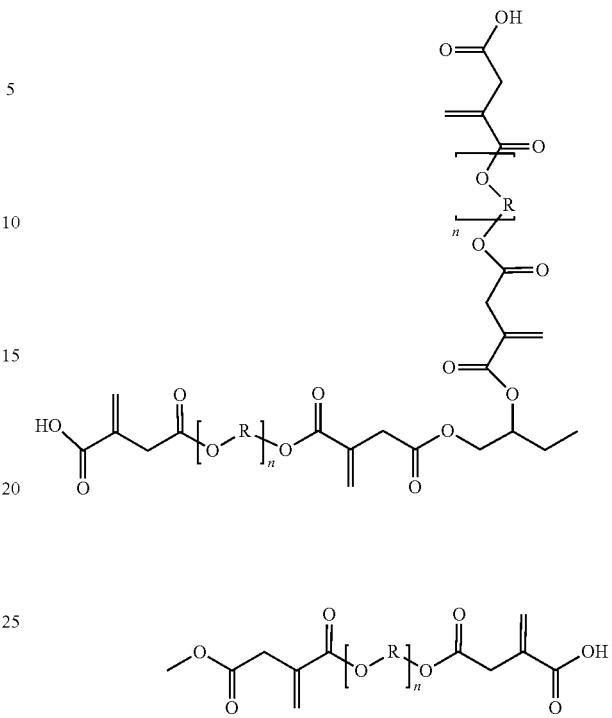

wherein R is selected from an alkyl group having 2-3 carbon atoms and n has a value in the range of 2-20.

2. The composition of claim 1 wherein there are 6-40 vinylidene groups.

3. The composition of claim 1 wherein said weight average molecular weight (Mw) is in the range of 950 g/mole to 30,000 g/mole.

4. The composition of claim 1 wherein said number average molecular weight (Mn) in the range of 800 g/mole to 10,000 g/mole.

5. The composition of claim 1 wherein said hydroxy terminated polyol has the following general structure;

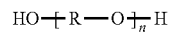

wherein R is an alkyl group having 2-3 carbon atoms and n has a value in the range of 2-20.

6. The composition of claim 1 wherein said multifunctional hydroxy compound has the following general structure:

wherein R is an alkyl group having 3-12 carbon atoms and n has a value greater than 2 up to 8.

7. The composition of claim 1 wherein said multifunctional hydroxy compound is selected from the group consisting of glycerol, glycerol, trimethyolpropane, xylitol, erythritol, maltitol, sorbitol, isomalt, and pentaerythritol.

8. The composition of claim 1 wherein said multifunctional hydroxy compound is selected from the group consisting of C-5 or C-6 carbohydrates.

9. The composition of claim 1 wherein said acid termination of said multibranched acid terminated oligomer is neutralized and is present as an acid salt.

10. The composition of claim 9 wherein said multibranched acid terminated oligomer present as an acid salt has the following structure:

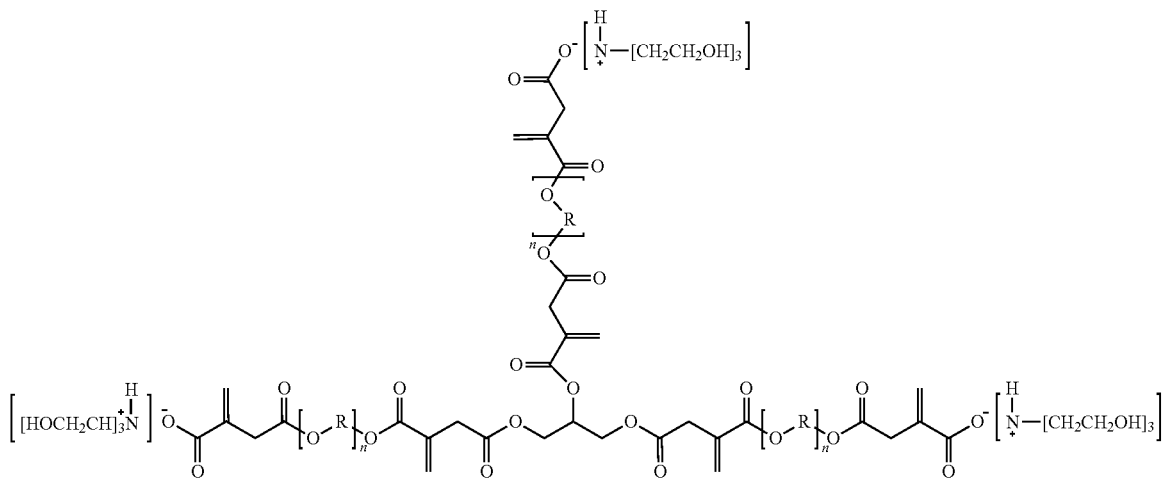

wherein R is selected from an alkyl group having 2-3 carbon atoms and n has a value in the range of 2-20.

11. A method of forming a multibranched acid terminated oligomer including 6 or more vinylidene groups comprising reacting itaconic acid, a hydroxy terminated polyol and a multifunctional hydroxy compound, in the presence of a free-radical inhibitor, wherein itaconic acid is present in molar excess to said hydroxy terminated polyol and said multifunctional hydroxy compound and forming said multibranched acid terminated oligomer including six or more vinylidene groups, wherein said oligomer is characterized by: (a) a maximum weight average molecular weight (Mw) of 30,000 g/mole; (b) a maximum number average molecular weight (Mn) of 10,000 g/mole; (c) an acid value of 100 mg KOH/gram to 250 mg KOH/gram; and (d) a hydroxyl value of less than or equal to 35 mg KOH/gram.

12. The method of claim 11 wherein said free-radical inhibitor is present at a level of 10 ppm to 3,000 ppm.

13. A method of treating hair comprising:
(1) supplying a multibranched acid terminated oligomer including 6 or more vinylidene groups, derived from itaconic acid, a hydroxy terminated polyol and a multifunctional hydroxy compound, wherein said oligomer is characterized by: (a) a maximum weight average molecular weight (Mw) of 30,000 g/mole; (b) a maximum number average molecular weight (Mn) of 10,000 g/mole; (c) an acid value of 100 mg KOH/gram to 250 mg KOH/gram; and (d) a hydroxyl value of less than or equal to 35 mg KOH/gram; and (2) treating hair with said multibranched acid terminated oligomer including 6 or more vinylidene groups.

14. A method of treating skin comprising:
(1) supplying a multibranched acid terminated oligomer including 6 or more vinylidene groups, derived from itaconic acid, a hydroxy terminated polyol and a multifunctional hydroxy compound, wherein said oligomer is characterized by: (a) a maximum weight average molecular weight (Mw) of 30,000 g/mole; (b) a maximum number average molecular weight (Mn) of 10,000 g/mole; (c) an acid value of 100 mg KOH/gram to 250 mg KOH/gram; and (d) a hydroxyl value of less than or equal to 35 mg KOH/gram; and (2) treating skin with said multibranched acid terminated oligomer including 6 or more vinylidene groups.

15. A composition comprising a multibranched acid terminated oligomer including 6 or more vinylidene groups, derived from itaconic acid, a hydroxy terminated polyol and a multifunctional hydroxy compound, wherein said oligomer is characterized by: (a) a maximum weight average molecular weight (Mw) of 30,000 g/mole; (b) a maximum number average molecular weight (Mn) of 10,000 g/mole; (c) an acid value of 100 mg KOH/gram to 250 mg KOH/gram; and (d) a hydroxyl value of less than or equal to 35 mg KOH/gram;

wherein said multibranched acid terminated oligomer including 6 or more vinylidene groups comprises the following structure:

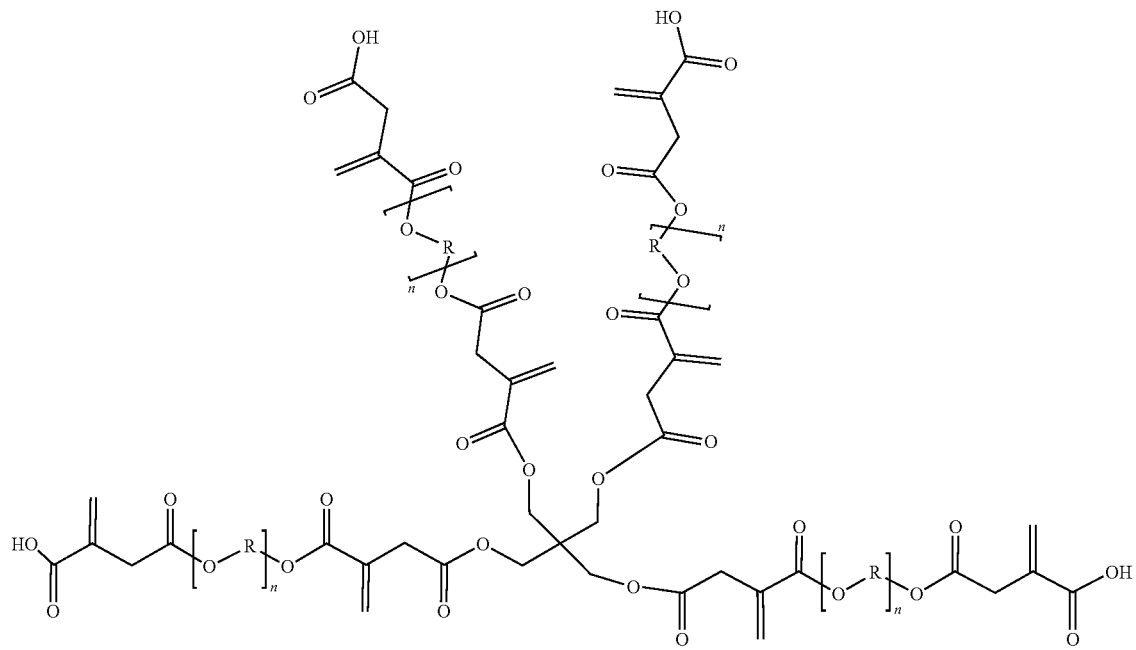

wherein R is selected from an alkyl group having 2-3 carbon atoms and n has a value in the range of 2-20.

16. A composition comprising a multibranched acid terminated oligomer including 6 or more vinylidene groups, derived from itaconic acid, a hydroxy terminated polyol and a multifunctional hydroxy compound, wherein said oligomer is characterized by: (a) a maximum weight average molecular weight (Mw) of 30,000 g/mole; (b) a maximum number average molecular weight (Mn) of 10,000 g/mole; (c) an acid value of 100 mg KOH/gram to 250 mg KOH/gram; and (d) a hydroxyl value of less than or equal to 35 mg KOH/gram;

wherein said multibranched acid terminated oligomer including six or more vinylidene groups comprises the following structure:

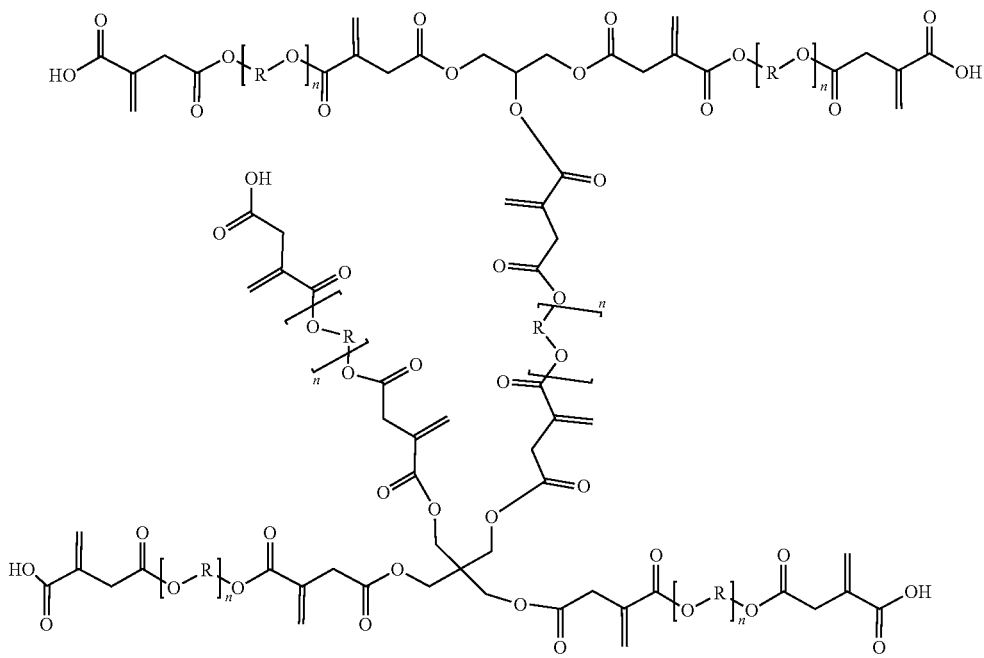

wherein R is selected from an alkyl group having 2-3 carbon atoms and n has a value in the range of 2-20.

* * * * *